United States Patent [19]

Anthony et al.

[11] Patent Number: 4,876,264
[45] Date of Patent: Oct. 24, 1989

[54] PYRIDINE DERIVATIVES AND THEIR USE AS FUNGICIDES

[75] Inventors: Vivienne M. Anthony, Maidenhead; John M. Clough, Marlow; Paul DeFraine, Wokingham; Christopher R. A. Godfrey, Bracknell, all of England

[73] Assignee: Imperial Chemical Industries PLC, London, England

[21] Appl. No.: 39,450

[22] Filed: Apr. 17, 1987

[30] Foreign Application Priority Data

Apr. 17, 1986 [GB] United Kingdom ................ 8609457
Jan. 22, 1987 [GB] United Kingdom ................ 8701395

[51] Int. Cl.$^4$ .................. A01N 43/40; C07D 213/70; C07D 213/71
[52] U.S. Cl. ..................... 514/345; 514/269; 514/274; 514/346; 514/347; 514/351; 546/291; 546/294; 546/300; 546/301; 546/302; 544/316; 544/318; 544/319; 544/398
[58] Field of Search ............. 546/291, 294, 300, 301, 546/302; 514/345, 346, 347, 351

[56] References Cited

FOREIGN PATENT DOCUMENTS

| 0178826 | 4/1986 | European Pat. Off. ............. 514/345 |
| 0203606 | 5/1986 | European Pat. Off. ............. 546/291 |
| 0203608 | 12/1986 | European Pat. Off. ............. 546/291 |
| 2521992 | 8/1983 | France ................................. 514/345 |
| 58-8063 | 1/1983 | Japan ................................. 514/345 |
| 1301817 | 1/1973 | United Kingdom ................ 514/345 |
| 2189485 | 10/1987 | United Kingdom ................ 546/301 |

OTHER PUBLICATIONS

Chem. Abstracts, vol. 105, No. 9; 78670z.
Chemical Abstracts, vol. 98, No. 8, 1983, p. 645, Abstract No. 179228d.

*Primary Examiner*—Richard A. Schwartz
*Assistant Examiner*—J. Richter
*Attorney, Agent, or Firm*—Cushman, Darby & Cushman

[57] ABSTRACT

Acrylic acid derivatives of the formula:

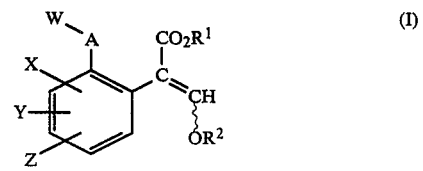

an stereoisomers thereof wherein W is pyridyl or pyrimidinyl, A is oxygen or $S(O)_n$ where n is 0, 1 or 2; X, Y and X are, for example, hydrogen, halogen, hydroxy or optionally substituted alkyl, alkenyl, alkynyl, alkoxy, aryl, aryloxy or aralkyl among other possible values; $R^1$ and $R^2$ are optionally substituted alkyl, and metal complexes thereof. The compounds are useful fungicides.

5 Claims, No Drawings

PYRIDINE DERIVATIVES AND THEIR USE AS FUNGICIDES

This invention relates to derivatives of acrylic acid useful as fungicides, to processes for preparing them, to fungicidal compositions containing them, and to methods of combating fungi, especially fungal infections in plants, using them.

The invention provides a compound having the general formula (I):

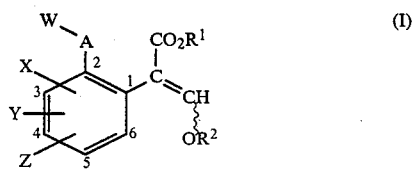

and stereoisomers thereof, wherein W is an unsubstituted pyridyl or unsubstituted pyrimidinyl group linked to A by any of its ring carbon atoms; A is either an oxygen atom or $S(O)_n$ wherein n is 0, 1 or 2; X, Y and Z, which are the same or different, are hydrogen or halogen atoms, or hydroxy, optionally substituted alkyl (including haloalkyl), optionally substituted alkenyl, optionally substituted alkynyl, optionally substituted alkoxy (including haloalkoxy), optionally substituted aryl, optionally substituted aryloxy, optionally substituted aralkyl, optionally substituted arylalkoxy, optionally substituted acyloxy, optionally substituted amino, optionally substituted acylamino, nitro, cyano, $-CO_2R^3$, $-CONR^4R^5$, $-COR^6$ or $-S(O)_nR^7$ (wherein n is 0, 1 or 2) groups, or any two of the groups X, Y and Z, when they are in adjacent positions on the phenyl ring, may join to form a fused ring, either aromatic or aliphatic, optionally containing one or more heteroatoms, provided that when A is oxygen, X is hydrogen, and $R^1$ and $R^2$ are both methyl, Y and Z are not both hydrogen, Y is not F, Cl, methyl, nitro, 5-$CF_3$, 5-$SCH_3$ or 4-$(CH_3)_2N$ if Z is hydrogen and Y and Z together are not 3-nitro-5-chloro, 3,5-dinitro, 4,5-dimethoxy or 4,5-methylenedioxy; $R^1$ and $R^2$, which are the same or different, are optionally substituted alkyl (including fluoroalkyl) groups; and $R^3$, $R^4$, $R^5$ and $R^6$, which are the same or different, are hydrogen atoms or optionally substituted alkyl, optionally substituted cycloalkyl, optionally substituted cycloalkylalkyl, optionally substituted alkenyl, optionally substituted alkynyl, optionally substituted aryl or optionally substituted aralkyl groups; and metal complexes thereof.

The compounds of the invention contain at least one carbon-carbon double bond, and are sometimes obtained in the form of mixtures of geometric isomers. However, these mixtures can be separated into individual isomers, and this invention embraces such isomers and mixtures thereof in all proportions including those which consist substantially of the (Z)-isomer and those which consist substantially of the (E)-isomer.

The individual isomers which result from the unsymmetrically substituted double bond of the acrylate group are hereinafter identified by the commonly used terms "E" and "Z". These terms are defined according to the Cahn-Ingold-Prelog system which is fully described in the literature (see, for example, J March, "Advanced Organic Chemistry," 3rd edition, Wiley-Interscience, page 109 et seq).

Usually one isomer is more fungicidally active than the other; the more active isomer being the one in which the group $-OR^2$ is on the same side of the double bond as the phenyl ring. In the case of the compounds of the present invention this is the (E)-isomer. The (E)-isomers form a preferred embodiment of the invention.

The formula:

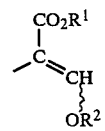

used hereinafter signifies a separable mixture of both geometric isomers about the acrylate double bond, i.e.

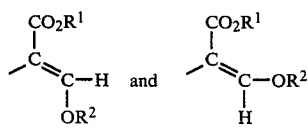

Halogen atoms, wherever referred to are particularly fluorine, chlorine or bromine atoms and especially fluorine or chlorine atoms.

Alkyl groups, and the alkyl moiety of alkoxy, aralkyl and arylalkoxy groups can be in the form of straight or branched chains, and contain preferably 1 to 6, more preferably 1 to 4, carbon atoms; examples are methyl, ethyl, propyl, (n- or iso-propyl), butyl (n-, sec-, iso- or t-butyl) and moieties thereof.

$R^1$ and $R^2$, which are optionally substituted alkyl groups, are preferably optionally substituted $C_{1-4}$, particularly $C_{1-2}$, alkyl groups. A preferred substituent is fluorine of which one or more atoms may be present. It is particularly preferred that $R^1$ and $R^2$ are both methyl, either one or both methyl groups being optionally substituted by one, two or three fluorine atoms.

Cycloalkyl groups include cyclohexyl, and cycloalkylalkyl groups include cyclopropylethyl. Alkenyl and alkynyl groups preferably contain 2 to 6, more preferably 2 to 4, carbon atoms in the form of straight or branched chains. Examples are ethenyl, allyl and propargyl. Aryl is preferably phenyl and aralkyl is preferably benzyl, phenylethyl or phenyl n-propyl. Optionally substituted alkyl includes in particular, haloalkyl, hydroxyalkyl, alkoxyalkyl, optionally substituted aralkyl, especially optionally substituted phenylalkyl, and optionally substituted aryloxyalkyl, especially optionally substituted phenoxyalkyl; optionally substituted alkenyl includes optionally substituted phenylalkenyl, especially optionally substituted phenylethenyl; optionally substituted aryloxy includes optionally substituted phenyloxy; and optionally substituted arylalkoxy includes optionally substituted benzyloxy.

Substituents which may be present in any optionally substituted aryl or heteroaryl moiety include one or more of the following; halogen, hydroxy, $C_{1-4}$ alkyl (especially methyl and ethyl), $C_{1-4}$ alkoxy (especially methoxy), halo($C_{1-4}$)alkyl (especially trifluoromethyl), halo($C_{1-4}$)alkoxy (especially trifluoromethoxy), $C_{1-4}$ alkylthio (especially methylthio), ($C_{1-4}$)alkoxy($C_{1-4}$)alkoxy($C_{1-4}$)alkyl, $C_{3-6}$ cycloalkyl, $C_{3-6}$ cycloalkyl($C_{1-4}$)alkyl, aryl (especially phenyl), aryloxy (especially phenyloxy), aryl($C_{1-4}$)alkyl (especially benzyl, phenylethyl and phenyl n-propyl), aryl($C_{1-4}$)alkoxy (especially benzyloxy), aryloxy($C_{1-4}$)alkyl (especially phenyloxymethyl), acyloxy (especially acetyloxy and benzoyloxy), cyano, thiocyanato, nitro, —NR'R", —NHCOR', —NHCONR'R", —CONR'R", —COOR', —OSO$_2$R', —SO$_2$R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$) alkyl, phenyl or benzyl, the phenyl and benzyl groups being optionally substituted with halogen, $C_{1-4}$ alkyl or $C_{1-4}$ alkoxy. Optionally substituted amino acylamino and acyloxy groups include the groups —NR'R", —NHCOR' and —OCOR' in which R' and R" are as defined above.

In one particular aspect, the invention provides compounds having the general formula (I):

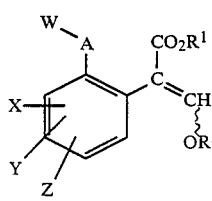

(I)

and stereoisomers thereof, wherein W is an unsubstituted pyridyl or unsubstituted pyrimidinyl group linked to A by any one of its ring carbon atoms; A is either an oxygen atom or S(O)$_n$ wherein n is 0, 1 or 2; X, Y and Z, which are the same or different, are hydrogen, fluorine, chlorine or bromine atoms, or hydroxy, $C_{1-4}$ alkyl, $C_{2-5}$ alkenyl, $C_{1-5}$ alkynyl, $C_{1-4}$ haloalkyl, $C_{1-4}$ alkoxy, phenyl, phenoxy, benzyl, benzyloxy, nitro, cyano, amino or mono- or dialkylamino groups, or any two of the groups X, Y and Z, when they are in adjacent positions on the phenyl ring, join to form a fused aromatic ring; wherein the aliphatic moieties of any of the foregoing are optionally substituted with one or more $C_{1-4}$ alkoxy groups, fluorine, chlorine or bromine atoms, phenyl rings which themselves are optionally substituted, heterocyclic rings which are either aromatic or non-aromatic and are themselves optionally substituted, nitro, amino, cyano, hydroxy or carboxy groups, and wherein the phenyl moieties of any of the foregoing are optionally substituted with one or more fluorine, chlorine or bromine atoms, optionally substituted phenyl rings, $C_{1-4}$ alkyl, $C_{1-4}$ alkoxy, nitro, amino, cyano, hydroxy or carboxy groups, provided that when A is oxygen, X is hydrogen, and R$^1$ and R$^2$ are both methyl, Y and Z are not both hydrogen, Y is not F, Cl, methyl, nitro, 5-CF$_3$, 5-SCH$_3$ or 4-(CH$_3$)$_2$N if Z is hydrogen and Y and Z together are not 3-nitro-5-chloro, 3,5-dinitro, 4,5-dimethoxy or 4,5-methylenedioxy; and R$^1$ and R$^2$, which are the same or different, are $C_{1-4}$ alkyl (especially both methyl), each optionally substituted with one, two or three halogen (especially fluorine), atoms.

Optional substituents in any phenyl or heterocyclic ring include those defined earlier in connection with aryl and heteroaryl moieties.

Heterocyclic rings include 2-, 3- and 4-pyridine rings and 2-, 4- and 5-pyrimidine rings.

It is preferred that X, Y and Z are single atoms or sterically small groups. Examples are hydrogen, fluorine, chlorine, bromine, hydroxy, methyl, methoxy, methylthio, trifluoromethyl, trifluoromethoxy, nitro, cyano, amino, methylamino, dimethylamino, carboxy, methylcarbonyl and methoxycarbonyl.

When only one of X, Y and Z is hydrogen, examples of combinations of the other two groups are, difluoro, dichloro, dibromo, chloro-nitro, dinitro, dimethoxy and methylenedioxy.

It is further preferred that when a substituent is present it occupies the 5-position of the phenyl ring (the acrylate group being attached to the 1-position) as this may confer an advantage with respect to phytotoxicity especially where there is present only a single substituent such as chlorine.

The invention especially provides compounds having the formula:

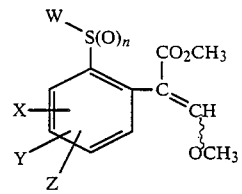

and stereoisomers thereof, wherein W is an unsubstituted pyridyl or unsubstituted pyrimidinyl group linked to the sulphur atom by any one of its ring carbon atoms; n is 0, 1 or 2; and X, Y and Z are selected from the group comprising hydrogen, fluorine, chlorine bromine, hydroxy, methyl, methoxy, methylthio, trifluoromethyl, trifluoromethoxy, nitro, amino, methylamino, and dimethylamino.

The invention also especially provides compounds having the formula:

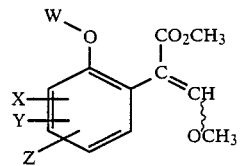

and stereoisomers thereof, wherein W is an unsubstituted pyridyl or unsubstituted pyrimidinyl group linked to the oxygen atom by one of its ring carbon atoms; and X, Y and Z are selected from the group comprising hydrogen, fluorine, chlorine, bromine, hydroxy, methyl, methoxy, methylthio, trifluoromethyl, trifluoromethoxy, nitro, amino, methylamino and dimethylamino, provided that X, Y and Z are not all hydrogen, that when two of X, Y and Z are hydrogen the other is bromo, hydroxy, trifluoromethoxy, amino or methylamino and that when one of X, Y and Z is hydrogen the remaining two are not 3-nitro-5-chloro, 3,5-dinitro or 4,5-dimethoxy.

The invention is illustrated by the compounds listed in Tables I and II below.

TABLE I

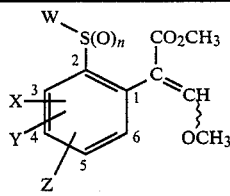

| Compound No. | W | n | X | Y | Z | Melting Point (°C.) | Olefinic* | Isomer + |
|---|---|---|---|---|---|---|---|---|
| 1 | Pyrid-2'-yl | 0 | H | 5-F | H | | | E |
| 2 | Pyrid-2'-yl | 0 | H | 5-Cl | H | | | E |
| 3 | Pyrid-2'-yl | 1 | H | 5-Br | H | | | E |
| 4 | Pyrid-2'-yl | 2 | H | 5-CH$_3$ | H | | | E |
| 5 | Pyrid-2'-yl | 0 | H | 5-OCH$_3$ | H | | | E |
| 6 | Pyrid-2'-yl | 0 | H | 5-OCF$_3$ | H | | | E |
| 7 | Pyrimidin-2'-yl | 0 | H | 5-F | H | | | E |
| 8 | Pyrimidin-2'-yl | 0 | H | 5-Cl | H | | | E |
| 9 | Pyrimidin-2'-yl | 0 | H | 5-Br | H | | | E |
| 10 | Pyrimidin-2'-yl | 0 | H | 5-CH$_3$ | H | | | E |
| 11 | Pyrimidin-2'-yl | 0 | H | 5-OCH$_3$ | H | | | E |
| 12 | Pyrimidin-2'-yl | 0 | H | 5-OCF$_3$ | H | | | E |
| 13 | Pyrid-3'-yl | 0 | H | 5-F | H | | | E |
| 14 | Pyrid-4'-yl | 0 | H | 5-F | H | | | E |
| 15 | Pyrimidin-4'-yl | 0 | H | 5-F | H | | | E |
| 16 | Pyrimidin-5'-yl | 0 | H | 5-F | H | | | E |
| 17 | Pyrid-2'-yl | 0 | H | 5-F | 6-F | | | E |
| 18 | Pyrid-2'-yl | 0 | H | H | 3-NO$_2$ | | | E |
| 19 | Pyrid-2'-yl | 0 | H | H | H | Oil | 7.47 | E |
| 20 | Pyrimidin-2'-yl | 0 | H | H | H | 114–117 | 7.50 | E |
| 21 | Pyrid-2'-yl | 0 | 3-F | 4-F | 5-F | | | E |
| 22 | Pyrid-3'-yl | 0 | H | H | H | | | E |
| 23 | Pyrid-4'-yl | 0 | H | H | H | | | E |
| 24 | Pyrimidin-4'-yl | 0 | H | H | H | | | E |
| 25 | Pyrimidin-5'-yl | 0 | H | H | H | | | E |

KEY:
*Chemical shift of singlet from olefinic proton on beta-methoxyacrylate group (ppm from tetramethylsilane). Solvent CDCl$_3$ unless otherwise stated.
+ Geometry of beta-methoxyacrylate group

TABLE II

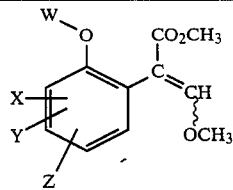

| Compound No | W | X | Y | Z | Melting Point (°C.) | Olefinic* | Isomer + |
|---|---|---|---|---|---|---|---|
| 1 | Pyrid-2'-yl | H | 5-Br | H | | | E |
| 2 | Pyrid-2'-yl | H | 5-Br | 6-Br | | | E |
| 3 | Pyrid-2'-yl | H | 5-OH | H | | | E |
| 4 | Pyrid-2'-yl | H | 4-NH$_2$ | H | | | E |
| 5 | Pyrid-2'-yl | H | 4-NHCH$_3$ | H | | | E |
| 6 | Pyrid-2'-yl | 3-Cl | 5-Br | H | | | E |
| 7 | Pyrimidin-2'-yl | H | 5-Br | H | | | E |
| 8 | Pyrimidin-2'-yl | 3-Br | H | H | | | E |
| 9 | Pyrimidin-2'-yl | H | 4-Br | H | | | E |
| 10 | Pyrimidin-2'-yl | H | H | 6-Br | | | E |
| 11 | Pyrimidin-2'-yl | 3-NO$_2$ | 5-Br | H | | | E |
| 12 | Pyrimidin-2'-yl | H | 5-OH | H | | | E |
| 13 | Pyrid-3'-yl | H | 5-Br | H | | | E |
| 14 | Pyrid-4'-yl | H | 5-Br | H | | | E |
| 15 | Pyrimidin-4'-yl | H | 5-Br | H | | | E |
| 16 | Pyrimidin-5'-yl | H | 5-Br | H | | | E |
| 17 | Pyrid-2'-yl | 3-F | 4-F | 5-F | | | E |
| 18 | Pyrid-2'-yl | 3-F | 5-F | 6-F | | | E |
| 19 | Pyrid-2'-yl | 4-F | 5-F | 6-F | | | E |
| 20 | Pyrid-2'-yl | 3-F | 5-Cl | 6-F | | | E |

*Chemical shift of singlet from olefinic proton on beta-methoxyacrylate group (ppm from tetramethylsilane). Solvent CDCl$_3$ unless otherwise stated.
+ Geometry of beta-methoxyacrylate group

TABLE III

TABLE III: Selected proton NMR data

Table III shows selected proton NMR data for certain compounds described in the foregoing Tables. Chemical shifts are measured in ppm from tetramethylsilane, and deuterochloroform was used as solvent. The following abbreviations are used:

| br = broad | t = triplet | ppm = parts per million |
|---|---|---|
| s = singlet | q = quartet | |
| d = doublet | m = multiplet | |

| Compound No. | |
|---|---|
| 19 (Table I) | 3.60 (3H,s); 3.72 (3H,s); 6.74–6.78 (1H,d); 6.90–6.95 (1H,m); 7.32–7.48 (5H,m, including one proton singlet at 7.47); 7.64–7.68 (1H,d); 8.36–8.40 (1H,d) ppm. |
| 20 (Table I) | 3.60 (3H,s); 3.75 (3H,s); 6.90–6.95 (1H,m); 7.32–7.55 (4H,m, including one proton singlet at 7.50); 7.70–7.75 (1H,d); 8.46–8.50 (1H,d) ppm. |

The compounds of the invention having the general formula (I) can be prepared from substituted phenols or thiophenols of general formula (VII) by the steps shown in Scheme I. Throughout Scheme I the terms $R^1$, $R^2$, A, X, Y, and Z are as defined above, L is a halogen atom or another good leaving group which can sometimes be a nitro group, and W is either an unsubstituted pyridyl or pyrimidinyl group or an activated derivative thereof (such as an N-oxide, halo or nitro derivative) which can subsequently be converted by standard reactions into an unsubstituted pyridyl or pyrimidinyl group and $R^8$ is hydrogen or a metal atom (especially an alkali metal atom such as a sodium atom).

Thus, compounds of general formula (I), which exist as geometric isomers which may be separated by chromatography, fractional crystallisation or distillation, can be prepared by treatment of phenylacetates of formula (IV) with a base (such as sodium hydride or sodium methoxide) and a formic ester such as methyl formate in a suitable solvent such as N,N-dimethylformamide and at a suitable temperature (step (b) of Scheme I). If a species of formula $R^2$-L, wherein L is as defined above, is then added to the reaction mixture, compounds of formula (I) may be obtained (step (a) of Scheme I). If a protic acid is added to the reaction mixture, compounds of formula (III) wherein $R^8$ is hydrogen are obtained. Alternatively, the species of formula (III) wherein $R^8$ is a metal atom (especially an alkali metal atom such as a sodium atom) may themselves be isolated from the reaction mixture.

Compounds of formula (III) wherein $R^8$ is a metal atom can be converted into compounds of formula (I) by treatment with a species of formula $R^2$-L, wherein L is as defined above, in a suitable solvent. Compounds of formula (III) wherein $R^8$ is hydrogen can be converted into compounds of formula (I) by successive treatment with a base (such as potassium carbonate) and a species of general formula $R^2$-L, in a suitable solvent.

Alternatively, compounds of general formula (I) can be prepared from acetals of general formula (XIII) by elimination of the appropriate alkanol under either acidic or basic conditions, at a suitable temperature and often in a suitable solvent (step (c) of Scheme I). Examples of reagents or reagent mixtures which can be used for this transformation are lithium di-isopropylamide; potassium hydrogen sulphate (see, for example, T Yamada, H Hagiwara and H Uda, *J. Chem. Soc., Chemical Communications*, 1980, 838, and references therein); and triethylamine, often in the presence of a Lewis acid such as titanium tetrachloride (see, for example, K Nsunda and L Heresi, *J. Chem. Soc., Chemical Communications*, 1985, 1000).

Acetals of general formula (XIII) can be prepared by treatment of alkyl silyl ketene acetals of general formula (XIV), wherein R is an alkyl group, with a trialkyl orthoformate in the presence of a Lewis acid such as titanium tetrachloride, at a suitable temperature and in a suitable solvent, such as dichloromethane (see, for example, K saigo, M Osaki and T Mukaiyama, *Chemistry Letters*, 1976, 769).

Alkyl silyl ketene acetals of general formula (XIV) can be prepared from esters of general formula (IV) by treatment with a base and a trialkylsilyl halide of general formula $R_3SiCl$ or $R_3SiBr$, such as trimethylsilyl chloride, or a base and a trialkylsilyl triflate of general formula $R_3Si$-$OSO_2CF_3$, in a suitable solvent (such as dichloromethane) and at a suitable temperature (see, for example, C Ainsworth, F Chen and Y Kuo, *J. Organometallic Chemistry*, 1972, 46, 59).

It is not always necessary to isolate the intermediates (XIII) and (XIV); under appropriate conditions, compounds of general formula (I) may be prepared from esters of general formula (IV) in a "one pot" sequence by the successive addition of suitable reagents listed above.

Compounds of general formula (IV) can be prepared by esterification of compounds of general formula (V) by standard methods described in the chemical literature (step (d) of Scheme I).

Compounds of general formula (V) can be prepared by the reaction of compounds of general formula (VII) with compounds of formula (VI) in the presence of a base (such as potassium carbonate) and, if necessary, a transition metal or transition metal salt catalyst (such as copper-bronze) in a convenient solvent (such as N,N-dimethylformamide) (Step (e) of Scheme I).

Alternatively, compounds of general formula (IV) can be prepared from esters of general formula (VIII) by reaction with compounds of general formula (VI) in the presence of a base (such as potassium carbonate) and, if necessary, a transition metal or transition metal salt catalyst (such as copper-bronze) in a convenient solvent (such as N,N-dimethylformamide) (Step (f) of Scheme I).

Esters of general formula (VIII) can be prepared by esterification of compounds of general formula (VII) by standard methods described in the chemical literature (Step (g) of Scheme I).

Compounds of general formula (VII) can be prepared by standard methods described in the chemical literature. (For example, see, A Clesse et al. *J. Med. Chem.*, 1981, 24, 1465 and P D Clark and D M McKinnon, *Can. J. Chem.*, 1982, 60, 243, and references therein).

Compounds of general formula (I) wherein A is sulphur may be converted into compounds of formula (I) wherein A is S(O) or S(O)$_2$ by standard methods of oxidation as described in the chemical literature, using, for example, a peracid such as meta-chloroperbenzoic acid, in a suitable solvent and at a suitable temperature.

Alternatively, compounds of the invention having the general formula (I) can be prepared from phenylacetates of general formula (XII) by the steps shown in Scheme II. Throughout Scheme II the terms $R^1$, $R^2$, A, W, X, Y, Z and L are as defined above, and P is a protecting group for a phenol or thiophenol group. Thus, compounds of general formula (I) can be prepared by reaction of compounds of general formula (IX) with compounds of general formula (VI) in the presence of a base (such as potassium carbonate) and, if necessary, a transition metal or transition metal salt catalyst in a convenient solvent (such as N,N-dimethylformamide) (step (h) of Scheme II).

Compounds of general formula (IX) can be prepared from protected phenol or thiophenol derivatives of general formula (X) by standard deprotection procedures as set out in the chemical literature (step (i) of Scheme II). For example, phenols of general formula (IX, A is O) can be prepared from benzyl ethers of general formula (X, A is O, P is CH$_2$Ph) by hydrogenolysis in the presence of a suitable catalyst (such as palladium supported on carbon).

Compounds of general formula (X), in which the group P is a standard phenol or thiophenol protecting group (such as benzyl), can be prepared by treatment of phenylacetates of formula (XII) with a base (such as sodium hydride or sodium methoxide) and a formic ester (such as methyl formate) in a suitable solvent such as N,N-dimethylformamide and at a suitable temperature (step (k) of Scheme II). If a species of formula R$^2$-L, wherein L is as defined above, is then added to the reaction mixture, compounds of formula (X) may be obtained (step (j) of Scheme II). If a protic acid is added to the reaction mixture, compounds of formula (XI) wherein R$^8$ is hydrogen are obtained. Alternatively, the species of formula (XI) wherein R$^8$ is a metal atom (especially an alkali metal atom such as a sodium atom) may themselves be isolated from the reaction mixture.

Compounds of formula (XI) wherein R$^8$ is a metal atom can be converted into compounds of formula (X) by treatment with a species of formula R$^2$-L, in a suitable solvent. Compounds of formula (XI) wherein R$^8$ is hydrogen can be converted into compounds of formula (X) by successive treatment with a base (such as potassium carbonate) and a species of formula R$^2$-L.

Compounds of general formula (XIII) can be prepared from compounds of general formula (VIII) by standard methods described in the chemical literature.

Scheme I

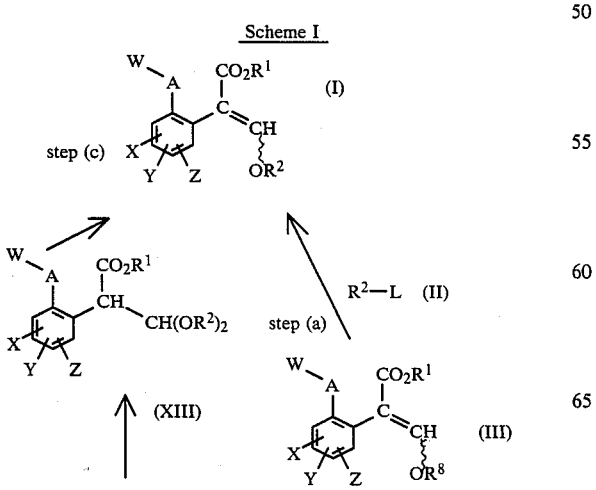

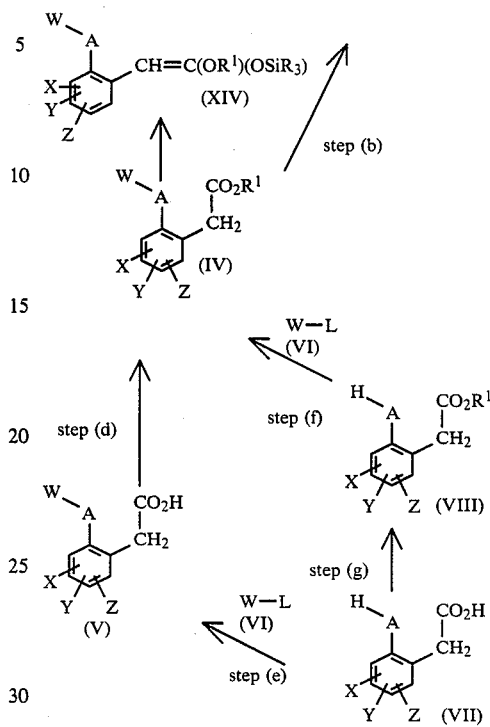

Scheme II

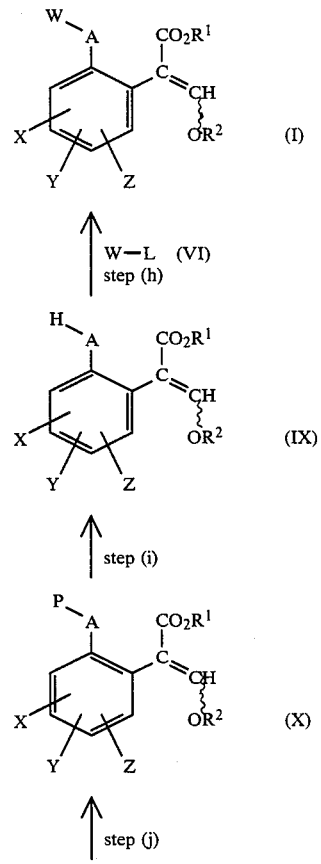

-continued
Scheme II

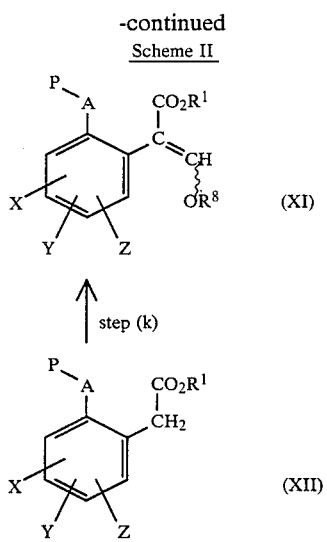

Scheme III

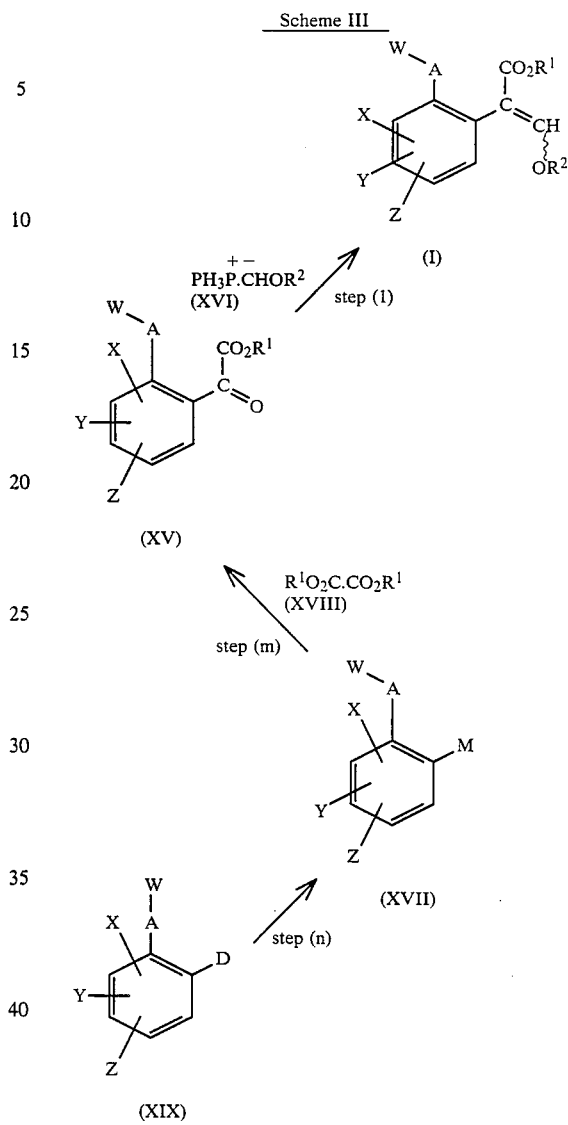

Alternatively, compounds of the invention having the general formula (I) can be prepared from substituted benzenes of general formula (XIX) by the steps shown in Scheme III. Throughout Scheme III the terms $R^1$, $R^2$, A, W, X, Y and Z are as defined above, D is a halogen (iodine, bromine or chlorine) or hydrogen and M is a metal atom (such as a lithium atom) or a metal atom plus an associated halogen atom (such as MgI, MgBr or MgCl).

Thus, compounds of general formula (I) can be prepared by treatment of ketoesters of general formula (XV) with phosphoranes of general formula (XVI) in a convenient solvent such as diethyl ether (see, for example, EP-A-0044448 and EP-A-0178826 (Step (c) of Scheme III).

Ketoesters of general formula (XV) can be prepared by treatment of metallated species (XVII) with an oxalate (XVIII) in a suitable solvent such as diethyl ether or tetrahydrofuran. The preferred method often involves slow addition of a solution of the metallated species (XVII) to a stirred solution of an excess of the oxalate (XVIII) (see, for example, L M Weinstock, R B Currie and A V Lovell, *Synthetic Communications*, 1981, 11, 943, and references therein) (step (m) of Scheme III).

The metallated species (XVII) in which M is MgI, MgBr or MgCl (Grignard reagents) can be prepared by standard methods from the corresponding aromatic halides (XIX) in which D is I, Br or Cl respectively. With certain substituents X, Y and Z, the metallated species (XVII) in which M is Li can be prepared by direct lithiation of compounds (XIX) in which D is H using a strong lithium base such as n-butyl-lithium or lithium di-isopropylamide (see, for example, H W Gachwend and H R Rodriquez, *Organic Reactions*, 1979, 26, 1) (step (n) of Scheme III).

Compounds of general formula (XIX) can be prepared by standard methods described in the chemical literature.

Alternative methods for the preparation of ketoesters of general formula (XV) are described in the chemical literature (see, for example, D C Atkinson, K E Godfrey, B Meek, J F Saville and M R Stillings, *J. Med. Chem.*, 1983, 26, 1353; D Horne, J Gaudino and W J Thompson, *Tetrahedron Lett.*, 1984, 25, 3529; and G P Axiotis, *Tetrahedron Lett.*, 1981, 22, 1509).

Methods for preparing compounds of the invention having the general formula (I), as described in Schemes I and II are generally applicable where W in general formula (I) is a 2-pyridyl, or a 2-, 4- or 5-pyrimidinyl group, However for compounds of general formula (I) where W is a 3- or 4-pyridyl group the methods shown in Scheme II may not be generally applicable.

Also, although compounds of the invention having the general formula (I) where W is a 3- or 4-pyridyl group may be prepared from compounds of general formula (IV) by steps (a), (b) and (c) as shown in Scheme I, the preparation of compounds of general formula (IV) where W is a 3- or 4-pyridyl group may not be generally prepared by the steps (e) and (f) in Scheme I. Therefore an alternative method of preparation of compounds of general formula (IV) may need to be used.

In general, compounds of formula (IV) where W is a 3- or 4-pyridyl group, may preferably be prepared by the route shown in Scheme IV.

Thus, in Scheme IV compounds of formula (IV) where W is a 3- or 4-pyridyl group can be prepared from compounds of formula (XX) where W is a 3-pyridyl or 4-pyridyl group.

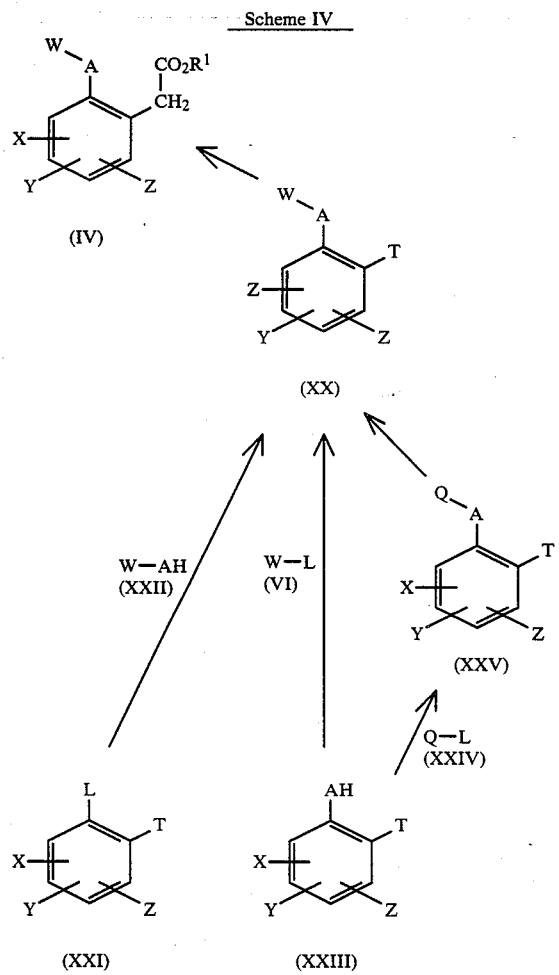

Throughout Scheme IV, A, X, Y, Z and L are as defined above for Schemes I–III and T is any group that can be converted by standard methods in the literature in one or more steps into, an acetic ester side chain of structure $CH_2COOR^1$ as shown in formula (IV). For example, T may be a formyl group or any group that is capable of being transformed into a formyl group, such as a formyl acetal which may be hydrolysed by aqueous acid to the formyl group or such as a nitrile which may be reduced to the formyl group by metal hydride reduction (see, for example, A E G Miller, J W Bliss and L H Schwartzmann, *J. Org. Chem.*, 1959, 24, 627) or by Raney Alloy in formic acid (see, for example, van Es and Staskun, *J. Chem. Soc.* 1965, 5775). When T is a formyl group, it may then be converted into the acetic ester residue $CH_2COOR^1$ by reaction with methyl methylsulphinylmethylsulphide ($CH_3SOCH_2SCH_3$) (see, for example, K Ogura and G Tsuchihashi, *Tetrahedron Lett.*, 1972, 1383-6), followed by hydrolysis with an alcohol $R^1OH$ in the presence of an acid such as hydrogen chloride. T may also be a group such as a methyl group which can be halogenated, for example by bromine or N-bromosuccinimide, to give a halomethyl group which can then be treated with cyanide ion to give a cyanomethyl group, which in turn can by hydrolysed to the acetic ester residue $CH_2COOR^1$ by methods well known in the literature. T may also be, for example, a carboxylic acid or ester group which may be reduced to a hydroxymethyl group, which in turn can be converted to a cyanomethyl group by methods well known in the literature.

Compounds of formula (XX), where W is a 3-pyridyl group, can be prepared from compounds of formula (XXI), where L is defined as for Scheme I, by reaction with compounds of formula (XXII), where W is a 3-pyridyl group, under conditions generally used for the well known Ullmann synthesis. For example the compounds of formula (XXI) can be treated with the metal salt (preferably the sodium or potassium salt) of the compounds of formula (XXII), either neat or in a suitable solvent such as N,N-dimethylformamide or dimethylsulphoxide at 50°–250° C., but preferably at 100°–180° C., in the presence of a transition metal catalyst such as copper bronze or copper halides.

Compounds of general formula (XXI) can be prepared by standard methods in the chemical literature.

Compounds of formula (XX), where W is a 4-pyridyl group, can be prepared by reaction of the metal salt (preferably the sodium or potassium salt) of compounds of formula (XXIII) with compounds of formula (VI), where W is a 4-pyridyl group, in a suitable solvent such as N,N-dimethylformamide or dimethylsulphoxide at 20°–200° C., but preferably at 50°–150° C., and optionally in the presence of transition metal catalysts such as copper bronze or copper halides.

Compounds of formula (XX) may also be prepared from compounds of formula (XXV), where Q is defined as a pyridine N-oxide linked to A through the 4-position. Deoxygenation of the N-oxide by standard methods, for example with phosphorus trichloride, will give compounds of formula (XX).

Compounds of formula (XXV) can be prepared by the reaction of the metal salt (preferably the sodium or potassium salt) of the compunds of formula (XXIII), with the compounds of formula (XXIV), wherein Q and L are as defined above, in a suitable solvent such as N,N-dimethylformamide or dimethylsulphoxide, at 20°–200° C. but preferably at 50°–150°, optionally in the presence of a transition metal catalyst such as copper bronze or copper halides. Compounds of formula (XXIII) can be prepared by standard methods in the chemical literature.

In further aspects, the invention provides processes as herein described for preparing the compounds of the invention and the intermediate chemicals of formulae (III)–(V), (IX)–(XV), (XVII), (XX) and (XXV) used therein.

The compounds are active fungicides, and may be used to control one or more of the following pathogens:

*Pyricularia oryzae* on rice, *Puccinia recondita, Puccinia striformis* and other rusts on wheat, *Puccinia hordei, Puccinia striiformis* and other rusts on barley, and rusts on other hosts e.g. coffee, pears, apples, peanuts, vegetables and oranmental plants. *Erysiphe graminis* (powdery mildew) on barley and wheat and other powdery mildews on various hosts such as *Sphaerotheca mucularis* on hops, *Sphaerotheca fuliginea* on cucurbits (e.g.

cucumber), *Podosphaera leucotricha* on applies and *Uncinula necator* on vines.

Helminthosporium spp., Rhynchosporium spp., Septoria spp. and *Pseudocercosporella herpotrichlides* on cereals. *Cercospora arachidicola* and *Cercosporidium personata* on peanuts and other Cercospora species on other hosts for example sugar beet, bananas, soya beans and rice. *Venturia inaequalis* (scab) on apples *Plasmopara viticola* on vines.

Other downy mildews such a *Bremia lactucae* on lettuce, Peronospora spp. on soybeans, tobacco, onions and other hosts and *Pseudoperonospora humuli* on hops and *Pseudoperonospora cubensis* on cucrubits *Phytophthora infestans* on potatoes and tomatoes and other Phytophthora spp. on vegetables, strawberries, avocado, pepper, ornamentals, tobacco, cocoa and other hosts.

Some of the compounds may be active as seed dressings against Fusarium spp., Septoria spp., Tilletia spp., (bunt, a seed borne disease of wheat), Ustilago spp., Helminthosporium spp. on cereals and *Pyricularia oryzae* on rice.

The compounds can move acropetally in the plant tissue. Moreover, they may be volatile enough to be active in the vapour phase against any fungi on the plant.

The compounds may also be useful as industrial (as opposed to agricultural) fungicides, e.g. in the prevention of fungal attack on wood, hides, leather and especially paint films.

The compounds may be used directly for fungicidal purposes but are more conveniently formulated into compositions using a carrier or diluent. The invention thus provides a fungicidal composition comprising a compound of general formula (I) as hereinbefore defined, and a fungicidally acceptable carrier or diluent.

The invention also provides a method of combating fungi, which comprises applying to a plant, to seed of a plant, or to the locus of the plant or seed, a compound as hereinbefore defined, or a composition containing the same.

The compounds, can be applied in a number of ways. For example they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichloroethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, eg. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (eg. nitrogen-, potassium- or phosphorus-containing fertilisers). Compositions comprising only granules of fertilizer incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants eg. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient. After dilution to form aqueous preparations, such preparations may contain varying amounts of the active ingredient depending upon the intended purpose, but an aqueous preparation containing from 0.01% to 10% by weight of active ingredient will normally be adequate.

The compositions of this invention may contain other compounds having biological activity, eg. compounds having similar to complementary fungicidal activity or which possess plant growth regulating, herbicidal or insecticidal activity.

A fungicidal compound which may be present in the composition of the invention may be one which is capable of combating ear diseases of cereals (eg. wheat) such as Septoria, Gibberella and Helminthosporium spp., seed and soil borne diseases and downy and powdery mildews on grapes and powdery mildew on scab on apple etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, 4-chloro-N-(cyanoethoxymethyl)benzamide, benalaxyl, fosetylaluminium, fenarimol, iprodione, prothiocarb, procymidone, vinclozolin, penconazole, myclobutanil, propamocarb, R0151297, diconazole, pyrazophos,ethirimol, ditalimfos, tridemorph, triforine, nuarimol, triazbutyl, guazatine, triacetate salt of 1,1'-iminodi(octamethylene)diguanidine, buthiobate, propiconazole, prochloraz, flutriafol, hexaconazole ie. the chemical 1-(1,2,4-triazole-1-yl)-2-(2,4-dichlorophenyl)hexan-2-ol, (2 RS, 3 RS)-2-(4-chlorophenyl)-3-cyclopropyl-1-(1H-1,2,4-triazol-1-yl)butan-2-ol, (RS)-1-(4-chloro-phenyl)-4,4-dimethyl-3-(1H-1,2,4-triazol-1-ylmethyl)pentan-3-ol, flusilazole, pyrifenox, triadimefon, triadimenol, dichlobutrazol, fenpropimorph, pyrifenox, fenpropidin, chlorozolinate, imazalil, fenfuram, carboxin, oxycarboxin, methfuroxam, dodemorph, BAS 454, blasticidin S, Kasugamycin, edifenphos, kitazin P, cycloheximide, phthalide, probenazole, isoprothiolane, tricyclazole, pyroquilon, chlorbenzthiazone, neoasozin, polyoxin D, validamycin A, mepronil, flutolanil, pencycuron, dichlomezine, phenazin oxide, nickel dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofosmethyl, pyroxyfurn, polyram, maneb, mancozeb, captafol, chlorothalonil, anilazine, thiram, captan, folpet, zineb, propineb, sulphur, dinocap, dichlorane, chlorane, binapacryl, nitrothal-isopropyl, dodine, dithianon, fentin hydroxide, fentin acetate, tecnazene, quintozene, dichloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofurna, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (eg. grasses).

Examples of suitable plant growth regulating compounds for use with the invention compounds are the gibberellins (eg. $GA_3$, $GA_4$ and $GA_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acid (eg. triiodobenzoic acid), morphactins (eg. chlorfluoroecol), maleic hydrazide, glyphosate, glyphosine, long chain fatty alcohols and acids, dikegulac, paclobutrazol, fluoridamid, mefluidide, substituted quaternary ammonium and phosphonium compounds (eg. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat, benzoylprop-ethyl 3,6-dichloropicolinic acid, fenpentezol, inabenfide, triapenthenol and tecnazene.

The following Examples illustrate the invention.

In the Examples, the term 'ether' refers to diethyl ether; chromatography was carried out using silica gel as the solid phase; magnesium sulphate was used to dry solutions; and reactions involving water-or air-sensitive intermediate were performed under nitrogen and in dried solvents.

Where shown, infrared and nmr data are selective; no attempt is made to list every absorption. The following abbreviations are used throughout:

| | |
|---|---|
| g = gramme(s) | delta = chemical shift |
| mmol = millimole(s) | $CDCl_3$ = deuterochloroform |
| ml = milliliter(s) | s = singlet |
| mmHg = Millimeters pressure of mercury | d = doublet |
| | t = triplet |

| | br = broad |
| --- | --- |
| | DMF = N,N—dimethyl-formamide |

EXAMPLE 1

This Example illustrates the preparation of (E)-methyl 2-[2'-pyrid-2"-ylthio)phenyl]-3-methoxyacrylate (Compound No. 19 of Table I).

A solution of the disodium salt of ortho-mercapto phenylacetic acid [formed by treatment of ortho-mercaptophenylacetic acid (4.2 g) in methanol (50 ml) with sodium hydroxide (2.0 g) followed by evaporation to dryness under reduced pressure] in DMF (50 ml) was added to potassium carbonate. A catalytic amount of copper bronze and a solution of 2-bromopyridine-N-oxide hydrochloride (5.25 g) in DMF were then added. The reaction mixture was heated to 100° C. for 4 hours, cooled and then poured into water (150 ml). The resultant mixture was carefully acidified with dilute hydrochloric acid and filtered. The aqueous filtrate was concentrated under reduced pressure to give a brown solid which was extracted with ethanol (200 ml) and filtered. The yellow filtrate was concentrated under reduced pressure to give 6.8 g of a brown gum which was treated with acidic methanol (50 ml) [from methanol (50 ml) and acetyl chloride (5 ml)] over a period of 2 days. The reaction mixture was concentrated under reduced pressure to give a brown oil which was taken up into water and neutralised with aqueous sodium hydrogen carbonate solution. The resultant pale green solution was extracted with ethyl acetate (×3) and then concentrated under reduced pressure. The residue was extracted into methanol, filtered and evaporated to give an orange gum. Trituration with dichloromethane gave a suspension which was filtered off.

The filtrate was then evaporated under reduced pressure to give a crude methyl 2'-(pyrid-2"-ylthio)phenylacetate N-oxide as an orange gum (1.8 g); infrared maximum at 1735 cm$^{-1}$.

The crude product (1.7 g) was treated with phosphorus trichloride (3.4 ml) in ethyl acetate (50 ml) at reflux. After 2.5 hours the reaction mixture was cooled, added to water, basified with aqueous sodium hydroxide solution, and then extracted with ethyl acetate (×3). The combined organic layers were washed with water (×2), dried, filtered and evaporated to give methyl 2'-(pyrid-2"-ylthio)phenylacetate as a yellow oil (1.4 g) (100% pure by glc analysis); infrared maximum 1735 cm$^{-1}$.

Trimethylsilyltriflate (1.21 ml) was added to a solution of triethylamine (0.86 ml) in ether (15 ml) over 2 minutes. The resultant cloudy suspension was stirred at room temperature for 15 minutes, and then added dropwise over 5 minutes at 0°-2° C. to a solution of methyl 2'-(pyrid-2"-ylthio)phenylacetate (1.3 g) in ether (25 ml). The reaction mixture was stirred at 0° C. for 1 hour, at room temperature for 1 hour and then left to stand overnight. Dichloromethane (10 ml) was added and the resultant solution added dropwise over 30 minutes at −65° C.−−70° C. to a second solution [formed previously by the addition of trimethylorthoformate (0.69 ml) in dichloromethane (20 ml) to titanium tetrachloride (0.69 ml) in dichloromethane (10 ml) at −65° C.]. The reaction mixture was stirred for a further 30 minutes at −65° C., 4 hours at room temperature, left to stand overnight, and the poured into 5% aqueous potassium carbonate. Extraction with ether (×2) gave, after drying and evaporation, a brown oil (0.4 g) which was chromatographed (eluent-ether) to afford (E)-methyl 2-[2'-(pyrid-2"-ylthio)phenyl]-3-methoxyacrylate as an orange oil (0.14 g) (100% pure by gc analysis); infrared maxima at 1700 and 1630 cm$^{-1}$, $^1$H NMR (CDCl$_3$) data as in Table III.

EXAMPLE 2

This Example describes the preparation of (E)-methyl 2-[2'-pyrimidin-2"-ylthio)phenyl]-3-methoxyacrylate (compound No. 20 of Table I).

To a solution of the disodium salt of orthomercaptophenylacetic acid [formed by treatment of orthomercaptophenylacetic acid (1.68 g) in methanol (15 ml) with sodium hydroxide (0.8 g) followed by evaporation to dryness] in DMF (25 ml) was added a catalytic amount of copper-bronze and a solution of 2-chloropyrimidine (2.29 g) in DMF (10 ml). The reaction mixture was stirred at room temperature overnight, poured into water, acidified with concentrated hydrochloric acid and then extracted with ether (×3). The combined ethereal extracts were washed with water (×2), dried and evaporated to give a yellow-green solid (0.33 g). The aqueous phases were further extracted with ethyl acetate to give after drying and evaporation a further 1.17 g of solid material. The combined results were dissolved in DMF (20 ml) and added to potassium carbonate (0.84 g). Dimethyl sulphate (0.58 ml) in DMF (5 ml) was added over 5 minutes at 0° C. and stirring continued. After 1 hour, the reaction mixture was added to water, and the resultant mixture was extracted with ether (×4). The combined ethereal extracts were washed with water (×2), dried and evaporated to give methyl [2'-(pyrimidin-2"-ylthio)phenyl]acetate as a yellow solid (1.30 g); mp. 58°-60° C.; infrared maximum 1725 cm$^{-1}$. Using the procedure outlined in the previous Example for converting the corresponding pyridylthiophenyl acetate to its acrylate derivative, methyl [2'-(pyrimidin-2"-ylthio)phenyl]acetate (1.30 g, gave (E)-methyl 2-[2'-(pyrimidin-2"-ylthio)phenyl]-3-methoxy-acrylate (0.13 g) was obtained as a yellow-brown gum (100% pure by gc analysis) which solidified on standing, mp. 114°-117° C.; infrared maxima 1700 and 1625 cm$^{-1}$, $^1$H NMR (CDCl$_3$) as in Table III.

The following are examples of compositions suitable for agricultural and horticultural purposes which can be formulated from the compounds of the invention. Such compositions form another aspect of the invention. Percentages are by weight.

EXAMPLE 3

An emulsifiable concentrate is made up by mixing and stirring the ingredients, until all are dissolved.

| | |
| --- | --- |
| Compound No. 19 of Table I | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 4

The active ingredient is dissolved in methylene dichloride and the resultant liquid sprayed onto the granules of attapulgite clay. The solvent is then allowed to evaporated to produce a granular composition.

| Compound No. 19 of Table I | 5% |
|---|---|
| Attapulgite granules | 95% |

EXAMPLE 5

A composition suitable for use as a seed dressing is prepared by grinding and mixing the three ingredients.

| Compound No. 20 of Table I | 50% |
|---|---|
| Mineral oil | 2% |
| China clay | 48% |

EXAMPLE 6

A dustable powder is prepared by grinding and mixing the active ingredient with talc.

| Compound No. 20 of Table I | 5% |
|---|---|
| Talc | 95% |

EXAMPLE 7

A suspension concentrate is prepared by ball milling the ingredients to form an aqueous suspension of the ground mixture with water.

| Compound No. 20 of Table I | 40% |
|---|---|
| Sodium lignosulphonate | 10% |
| Bentonite clay | 1% |
| Water | 49% |

This formulatiion can be used as a spray by diluting into water or applied directly to seed.

EXAMPLE 8

A wettable powder formulation is made by mixing and grinding the ingredients until all are thoroughly mixed.

| Compound No. 20 of Table I | 25% |
|---|---|
| Sodium lauryl sulphate | 2% |
| Sodium lignosulphonate | 5% |
| Silica | 25% |
| China clay | 43% |

EXAMPLE 9

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erisiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4=no disease
3=trace-5% of disease on untreated plants
2=6-25% of disease on untreated plants
1=26-59% of disease on untreated plants
0=60-100% of disease on untreated plants The results are shown in Table IV.

TABLE IV

| COMPOUND NO. | PUCCINIA RECONDITA (WHEAT) | ERYSIPHE GRAMINIS HORDEI (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INFESTANS (TOMATO) |
|---|---|---|---|---|---|---|---|
| 19 | 4 | 4 | 4 | 3 | 4 | 4 | 0 |
| 20 | 4 | 4 | 4 | 0 | 4 | 4 | 4 |

We claim:

1. A compound having the formula (I):

and stereoisomers thereof, wherein W is an unsubstituted pyridyl group linked to A by one of its ring carbon atoms; A is $S(O)_n$ wherein n is 0, 1 or 2; X, Y and Z, which are the same or different, are hydrogen or halogen atoms, or hydroxy, $C_{1-6}$ alkyl (optionally substituted with one or more of hydroxy, halogen, $C_{1-4}$ alkoxy), $C_{2-6}$ alkenyl (optionally substituted with phenyl), $C_{2-6}$ alkynyl, $C_{1-6}$ alkoxy, phenyl, phenoxy, phenyl($C_{1-4}$)alkyl, phenyl($C_{1-4}$)alkoxy, $C_{1-6}$ alkanoyloxy, benzoyloxy, amino, $C_{1-4}$ alkylamino, di($C_{1-4}$)alkylamino, $C_{1-6}$ alkanoylamino, nitro, cyano, $-CO_2R^3$, $-CONR^4R^5$, $-COR^6$ or $-S(O)_mR^7$ (wherein m is 0, 1 or 2) groups, the alkyl moieties of any of the foregoing groups being optionally substituted with one or more of hydroxy, halogen or $C_{1-4}$ alkoxy, the phenyl moieties of any of the foregoing groups being optionally substituted with one or more of halogen, hydroxy, $C_{1-4}$ alkyl, $C_{1-4}$ alkoxy, halo($C_{1-4}$)alkyl, $C_{1-4}$ alkylthio, $C_{1-4}$ alkoxy($C_{1-}$ 4)alkyl, $C_{3-6}$ cycloalkyl, $C_{3-6}$ cycloalkyl($C_{1-4}$)alkyl, phenyl, phenoxy, phenyl($C_{1-4}$)alkyl, phenyl($C_{1-4}$)alkoxy, phenoxy($C_{1-4}$)alkyl, $C_{1-6}$ alkanoyloxy, benzoyloxy, cyano, thiocyanato, nitro, —NR'R", —NHCOR', —NHCONR'R", —CONR'R", —COOR', —O—SO$_2$R', —SO$_2$R', —COR', —CR'=NR", or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl or benzyl groups being optionally substituted with halogen, $C_{1-4}$ alkyl or $C_{1-4}$ alkoxy; $R^1$ and $R^2$ which are the same or different are $C_{1-4}$ alkyl optionally substituted by halogen; and $R^3$, $R^4$, $R^5$ and $R^6$, which are the same or different, are hydrogen atoms, $C_{1-6}$ alkyl, $C_{3-6}$ cycloalkyl, $C_{3-6}$ cycloalkyl($C_{1-6}$)alkyl, $C_{2-6}$ alkenyl, $C_{2-6}$ alkynyl, phenyl or phenyl($C_{1-6}$)alkyl in which the phenyl and alkyl moieties are optionally substituted as defined above.

2. A compound having the formula (I):

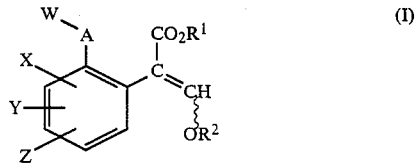

(I)

and stereoisomers thereof, wherein W is an unsubstituted pyridyl group linked to A by any one its ring carbon atoms; A is S(O)$_n$ wherein n is 0, 1 or 2; X, Y and Z, which are the same or different, are hydrogen, fluorine, chlorine or bromine atoms, or hydroxy, $C_{1-4}$ alkyl, $C_{2-5}$ alkenyl, $C_{2-5}$ alkynyl, $C_{1-4}$ haloalkyl, $C_{1-4}$ alkoxy, phenyl, phenoxy, benzyl, benzyloxy, nitro, cyano, amino or mono- or di-$C_1$-$C_4$ alkylamino groups wherein the aliphatic moieities of any of the foregoing are optionally substituted with one or more $C_{1-4}$ alkoxy groups, fluorine, chlorine or bromine atoms, phenyl rings which themselves are optionally substituted, nitro, amino, cyano, hydroxy or carboxy groups, and wherein the phenyl moieties of any of the foregoing are optionally substituted with one or more fluorine, chlorine or bromine atoms, phenyl rings, $C_{1-4}$ alkyl, $C_{1-4}$ alkoxy, nitro, amino, cyano, hydroxy or carboxy groups, and $R^1$ and $R^2$, which are the same or different, are $C_{1-4}$ alkyl, each optionally substituted with one, two or three halogen atoms.

3. A compound having the formula:

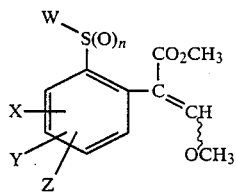

and stereoisomers thereof, wherein W is an unsubstituted pyridyl group linked to the sulphur atom by any one of its ring carbon atoms; n is 0, 1 or 2; and X, Y and Z are selected from the group comprising hydrogen, fluorine, chlorine, bromine, hydroxy, methyl, methoxy, methylthio, trifluoromethyl, trifluoromethoxy, nitro, amino, methylamino, and dimethylamino.

4. A fungicidal composition comprising, as an active ingredient, a fungicidally effective amount of a compound according to claim 1 and a fungicidally acceptable carrier or diluent therefor.

5. A method of combating fungi which comprises applying to plants or seeds, or to their locus, a compound according to claim 1.

* * * * *